(12) United States Patent  (10) Patent No.: US 8,734,464 B2
Grover et al.  (45) Date of Patent: May 27, 2014

(54) SURGICAL RETRIEVAL APPARATUS FOR THORACIC PROCEDURES

(75) Inventors: Simon Roderick Grover, Cambridge (GB); Oliver Brian Godbold, Cambridge (GB); Alistair Ian Fleming, Lower Cambourne (GB)

(73) Assignee: Covidien LP, Mansfield, MA (US)

( * ) Notice: Subject to any disclaimer, the term of this patent is extended or adjusted under 35 U.S.C. 154(b) by 133 days.

(21) Appl. No.: 13/235,597

(22) Filed: Sep. 19, 2011

(65) Prior Publication Data

US 2012/0179165 A1  Jul. 12, 2012

Related U.S. Application Data

(60) Provisional application No. 61/430,208, filed on Jan. 6, 2011.

(51) Int. Cl.
*A61B 17/24* (2006.01)

(52) U.S. Cl.
USPC .......................................... 606/114

(58) Field of Classification Search
USPC ......... 606/114, 127, 128, 141, 142, 108, 200; 623/1.11, 1.12; 600/562; 604/317, 540
See application file for complete search history.

(56) References Cited

U.S. PATENT DOCUMENTS

| | | |
|---|---|---|
| 30,471 A | 10/1860 | Dudley |
| 35,164 A | 5/1862 | Logan et al. |
| 156,477 A | 11/1874 | Bradford |
| 1,609,014 A | 11/1926 | Dowd |
| 3,800,781 A | 4/1974 | Zalucki |
| 4,557,255 A | 12/1985 | Goodman |
| 4,611,594 A | 9/1986 | Grayhack et al. |
| 4,744,363 A | 5/1988 | Hasson |
| 4,790,812 A | 12/1988 | Hawkins, Jr. et al. |
| 4,927,427 A | 5/1990 | Kriauciunas et al. |
| 4,997,435 A | 3/1991 | Demeter |
| 5,037,379 A | 8/1991 | Clayman et al. |
| 5,074,867 A | 12/1991 | Wilk |

(Continued)

FOREIGN PATENT DOCUMENTS

| | | |
|---|---|---|
| DE | 8435489 | 12/1984 |
| DE | 3542667 | 6/1986 |

(Continued)

OTHER PUBLICATIONS

European Search Report EP 12 15 0271 dated Jan. 14, 2013.

(Continued)

*Primary Examiner* — Ryan Severson
*Assistant Examiner* — Anh Dang

(57) ABSTRACT

A surgical retrieval apparatus includes a housing defining a longitudinal axis and including an elongated sleeve extending distally therefrom. The housing and the elongated sleeve cooperate to define a lumen extending longitudinally therethrough. A shaft having an end effector disposed at a distal end thereof is selectively translatable between a first position, wherein the end effector is disposed within the elongated sleeve, and a second position, wherein the shaft is translated through the lumen such that the end effector extends distally from the elongated sleeve. An articulation mechanism operably coupled to the end effector is configured for articulating the end effector relative to the longitudinal axis. A specimen retrieval bag is coupled to the end effector and is deployed therefrom upon movement of the end effector from the first position to the second position.

5 Claims, 12 Drawing Sheets

(56) References Cited

U.S. PATENT DOCUMENTS

| | | | |
|---|---|---|---|
| 5,084,054 A | 1/1992 | Bencini et al. |
| 5,143,082 A | 9/1992 | Kindberg et al. |
| 5,147,371 A | 9/1992 | Washington et al. |
| 5,176,687 A | 1/1993 | Hasson et al. |
| 5,190,542 A | 3/1993 | Nakao et al. |
| 5,190,555 A | 3/1993 | Wetter et al. |
| 5,190,561 A | 3/1993 | Graber |
| 5,192,284 A | 3/1993 | Pleatman |
| 5,192,286 A | 3/1993 | Phan et al. |
| 5,201,740 A | 4/1993 | Nakao et al. |
| 5,215,521 A | 6/1993 | Cochran et al. |
| 5,234,439 A | 8/1993 | Wilk et al. |
| 5,279,539 A | 1/1994 | Bohan et al. |
| 5,312,416 A | 5/1994 | Spaeth et al. |
| 5,330,483 A | 7/1994 | Heaven et al. |
| 5,336,227 A | 8/1994 | Nakao et al. |
| 5,337,754 A | 8/1994 | Heaven et al. |
| 5,341,815 A | 8/1994 | Cofone et al. |
| 5,352,184 A | 10/1994 | Goldberg et al. |
| 5,354,303 A | 10/1994 | Spaeth et al. |
| 5,368,545 A | 11/1994 | Schaller et al. |
| 5,368,597 A | 11/1994 | Pagedas |
| 5,370,647 A | 12/1994 | Graber et al. |
| 5,443,472 A | 8/1995 | Li |
| 5,465,731 A | 11/1995 | Bell et al. |
| 5,480,404 A | 1/1996 | Kammerer et al. |
| 5,486,182 A | 1/1996 | Nakao et al. |
| 5,486,183 A | 1/1996 | Middleman et al. |
| 5,499,988 A | 3/1996 | Espiner et al. |
| 5,524,633 A | 6/1996 | Heaven et al. |
| 5,535,759 A | 7/1996 | Wilk |
| 5,578,048 A * | 11/1996 | Pasqualucci et al. ......... 606/192 |
| 5,611,803 A | 3/1997 | Heaven et al. |
| 5,618,296 A | 4/1997 | Sorensen et al. |
| 5,630,822 A | 5/1997 | Hermann et al. |
| 5,643,282 A | 7/1997 | Kieturakis |
| 5,643,283 A | 7/1997 | Younker |
| 5,645,083 A | 7/1997 | Essig et al. |
| 5,647,372 A | 7/1997 | Tovey et al. |
| 5,649,902 A | 7/1997 | Yoon |
| 5,658,296 A | 8/1997 | Bates et al. |
| 5,679,423 A | 10/1997 | Shah |
| 5,735,289 A | 4/1998 | Pfeffer et al. |
| 5,755,724 A | 5/1998 | Yoon |
| 5,759,187 A | 6/1998 | Nakao et al. |
| 5,769,794 A | 6/1998 | Conlan et al. |
| 5,785,677 A | 7/1998 | Auweiler |
| 5,788,709 A | 8/1998 | Riek et al. |
| 5,792,145 A | 8/1998 | Bates et al. |
| 5,814,044 A | 9/1998 | Hooven |
| 5,836,953 A | 11/1998 | Yoon |
| 5,853,374 A | 12/1998 | Hart et al. |
| 5,895,392 A | 4/1999 | Riek et al. |
| 5,906,621 A | 5/1999 | Secrest et al. |
| 5,944,727 A * | 8/1999 | Ahari et al. .................. 606/108 |
| 5,957,884 A | 9/1999 | Hooven |
| 5,971,995 A | 10/1999 | Rousseau |
| 5,980,544 A | 11/1999 | Vaitekunas |
| 5,997,547 A | 12/1999 | Nakao et al. |
| 6,004,330 A | 12/1999 | Middleman et al. |
| 6,007,512 A | 12/1999 | Hooven |
| 6,019,770 A | 2/2000 | Christoudias |
| 6,036,681 A | 3/2000 | Hooven |
| 6,059,793 A | 5/2000 | Pagedas |
| 6,123,701 A | 9/2000 | Nezhat |
| 6,152,932 A | 11/2000 | Ternström |
| 6,162,235 A | 12/2000 | Vaitekunas |
| 6,165,121 A | 12/2000 | Alferness |
| 6,168,603 B1 | 1/2001 | Leslie et al. |
| 6,228,095 B1 | 5/2001 | Dennis |
| 6,270,505 B1 | 8/2001 | Yoshida et al. |
| 6,277,083 B1 | 8/2001 | Eggers et al. |
| 6,280,450 B1 | 8/2001 | McGuckin, Jr. |
| 6,344,026 B1 | 2/2002 | Burbank et al. |
| 6,348,056 B1 | 2/2002 | Bates et al. |
| 6,350,266 B1 | 2/2002 | White et al. |
| 6,350,267 B1 | 2/2002 | Stefanchik |
| 6,383,195 B1 | 5/2002 | Richard |
| 6,383,196 B1 | 5/2002 | Leslie et al. |
| 6,383,197 B1 | 5/2002 | Conlon et al. |
| 6,406,440 B1 | 6/2002 | Stefanchik |
| 6,409,733 B1 | 6/2002 | Conlon et al. |
| 6,419,639 B2 | 7/2002 | Walther et al. |
| 6,447,523 B1 | 9/2002 | Middleman et al. |
| 6,471,659 B2 | 10/2002 | Eggers et al. |
| 6,506,166 B1 | 1/2003 | Hendler et al. |
| 6,508,773 B2 | 1/2003 | Burbank et al. |
| 6,537,273 B1 | 3/2003 | Sosiak et al. |
| 6,589,252 B2 | 7/2003 | McGuckin, Jr. |
| 6,752,811 B2 | 6/2004 | Chu et al. |
| 6,755,779 B2 | 6/2004 | Vanden Hoek et al. |
| 6,780,193 B2 | 8/2004 | Leslie et al. |
| 6,805,699 B2 | 10/2004 | Shimm |
| 6,840,948 B2 | 1/2005 | Albrecht et al. |
| 6,872,211 B2 | 3/2005 | White et al. |
| 6,887,255 B2 | 5/2005 | Shimm |
| 6,994,696 B2 | 2/2006 | Suga |
| 7,052,454 B2 | 5/2006 | Taylor |
| 7,052,501 B2 | 5/2006 | McGuckin, Jr. |
| 7,090,637 B2 | 8/2006 | Danitz et al. |
| 7,270,663 B2 | 9/2007 | Nakao |
| 7,273,488 B2 | 9/2007 | Nakamura et al. |
| 7,410,491 B2 | 8/2008 | Hopkins et al. |
| 7,547,310 B2 | 6/2009 | Whitfield |
| 7,837,612 B2 | 11/2010 | Gill et al. |
| 2003/0100919 A1 | 5/2003 | Hopkins et al. |
| 2004/0097960 A1 | 5/2004 | Terachi et al. |
| 2004/0138587 A1 | 7/2004 | Lyons |
| 2005/0267492 A1 | 12/2005 | Poncet et al. |
| 2006/0052799 A1 | 3/2006 | Middleman et al. |
| 2006/0058776 A1 | 3/2006 | Bilsbury |
| 2006/0200169 A1 | 9/2006 | Sniffin |
| 2006/0200170 A1 | 9/2006 | Aranyi |
| 2006/0229639 A1 | 10/2006 | Whitfield |
| 2006/0229640 A1 | 10/2006 | Whitfield |
| 2007/0016224 A1 | 1/2007 | Nakao |
| 2007/0016225 A1 | 1/2007 | Nakao |
| 2007/0073251 A1 | 3/2007 | Zhou et al. |
| 2007/0088370 A1 | 4/2007 | Kahle et al. |
| 2007/0135780 A1 | 6/2007 | Pagedas |
| 2007/0135781 A1 | 6/2007 | Hart |
| 2008/0188766 A1 | 8/2008 | Gertner |
| 2008/0221588 A1 | 9/2008 | Hollis et al. |
| 2008/0234696 A1 | 9/2008 | Taylor et al. |
| 2008/0300621 A1 | 12/2008 | Hopkins et al. |
| 2008/0312496 A1 | 12/2008 | Zwolinski |
| 2009/0082779 A1 | 3/2009 | Nakao |
| 2009/0182292 A1 | 7/2009 | Egle et al. |
| 2009/0192510 A1 | 7/2009 | Bahney |
| 2009/0192518 A1 * | 7/2009 | Golden et al. ................ 606/108 |
| 2009/0240238 A1 | 9/2009 | Grodrian et al. |
| 2010/0000471 A1 | 1/2010 | Hibbard |

FOREIGN PATENT DOCUMENTS

| | | |
|---|---|---|
| EP | 1707126 A1 | 10/2006 |
| EP | 2184014 | 5/2010 |
| FR | 1272412 | 9/1961 |
| WO | WO 93/15675 | 8/1993 |
| WO | WO 95/09666 | 4/1995 |
| WO | WO 2004/002334 A1 | 1/2004 |
| WO | WO 2005/112783 A1 | 12/2005 |
| WO | 2007/048078 A1 | 4/2007 |
| WO | 2009/149146 A1 | 12/2009 |

OTHER PUBLICATIONS

European Search Report 12 19 3450 dated Feb. 27, 2013.

* cited by examiner

SURGICAL RETRIEVAL APPARATUS FOR THORACIC PROCEDURES

This application claims priority from provisional application Ser. No. 61/430,208, filed Jan. 6, 2011, the entire contents of which are incorporated herein by reference.

BACKGROUND

1. Technical Field

The present disclosure relates to a retrieval apparatus, and more particularly, to a surgical retrieval apparatus for use in thoracic surgical procedures.

2. Background of Related Art

In minimally invasive surgical procedures, operations are carried out within the body by using elongated instruments inserted through small entrance openings in the body. The initial opening in the body tissue to allow passage of instruments to the interior of the body may be a natural passageway of the body, or it can be created by a tissue piercing instrument such as a trocar, or created by a small incision into which a cannula is inserted.

Because the tubes, instrumentation, and any required punctures or incisions are relatively small, the surgery is less invasive as compared to conventional surgical procedures in which the surgeon is required to cut open large areas of body tissue. Therefore, minimally invasive surgery minimizes trauma to the patient and reduces patient recovery time and hospital costs.

Minimally invasive procedures may be used for partial or total removal of body tissue or organs from the interior of the body, e.g. nephrectomy, cholecystectomy, lobectomy and other procedures including thoracic, laparoscopic and endoscopic procedures. During such procedures, it is common that a cyst, tumor, or other affected tissue or organ needs to be removed via the access opening in the skin, or through a cannula. Various types of entrapment devices have been disclosed to facilitate this procedure. In many procedures where cancerous tumors are removed, removal of the specimen in an enclosed environment is highly desirable to prevent seeding of cancer cells.

In minimally invasive thoracic surgery, access to the thoracic cavity is limited as well as maneuverability within the cavity as the access port is placed between the confined space between a patient's ribs. Such procedures, commonly referred to as video assisted thoracoscopic surgery (VATS), aim to reduce patient recovery time by accessing the thoracic cavity through the natural intercostal space without spreading the ribs as in open procedures. This restricted access can sometimes cause problems when removing large specimens. Moreover, in such procedures, e.g. thoracoscopic wedge resection and lobectomy, it is often necessary to remove a portion of the lung and retrieve it relatively intact for pathology. It is also important that the specimen be sufficiently contained to prevent seeding of cancer cells during manipulation and removal.

In designing such specimen retrieval instrumentation, a balance must be struck between the need to provide a retrieval apparatus with a strong enough containment bag to prevent tearing or rupture while providing sufficient rigidity to enable manipulation and removal. Another balance which needs to be achieved is to provide sufficient maneuverability while reducing tissue trauma, e.g. damaging lung tissue, during manipulation and removal. Additionally, the instrumentation on one hand should be able to be inserted through a small access incision or port while on the other hand able to accommodate a wide range of patient sizes and be able to easily remove large specimens and minimize risk of seeding.

SUMMARY

In accordance with one aspect of the present disclosure, a surgical retrieval apparatus is provided. The surgical retrieval apparatus in one aspect includes a housing defining a longitudinal axis and having an elongated sleeve extending distally therefrom. The housing and the elongated sleeve cooperate to define a lumen extending longitudinally therethrough. A shaft having an end effector assembly disposed at a distal end thereof is configured for selective translation through the lumen of the housing and elongated sleeve between a first position and a second position. In the first position, the end effector assembly is disposed within the elongated sleeve. In the second position, the shaft is translated distally through the lumen such that the end effector assembly extends distally from the elongated sleeve. An articulation mechanism coupled to the end effector assembly is configured for selectively articulating the end effector assembly with respect to the longitudinal axis when the shaft is disposed in the second position. Articulation of the end effector assembly is inhibited when the shaft is disposed in the first position. A specimen retrieval bag is coupled to the end effector assembly. The specimen retrieval bag is deployed from an un-deployed, or retracted position, to an extended position upon movement of the end effector assembly from the first position to the second position.

In some embodiments, the shaft is manually translatable between the first and second positions, i.e., the shaft may be selectively translated by a hand of the clinician.

In some embodiments, a locking mechanism (or locking mechanisms) is provided for retaining the shaft in the first position and/or the second position.

In some embodiments, a release trigger may be provided, e.g., disposed on the housing, such that, upon actuation, the shaft is released, or unlocked, permitting the clinician to manually translate the shaft from the second position back to the first position. Further, in such embodiments, upon actuation of the release trigger, a plunger may be extended proximally from the shaft to facilitate manual translation of the shaft from the second position back to the first position, e.g., via grasping the plunger.

In some embodiments, the specimen retrieval bag is released from the end effector assembly upon translation of the shaft from the second position back to the first position. Additionally, an interference member may be provided to inhibit the specimen retrieval bag from being retained on the end effector assembly upon translation of the shaft from the second position back to the first position.

In some embodiments, a cinch cord is coupled at a distal end thereof to an open end of the specimen retrieval bag and is releasably engaged at a proximal end thereof to the shaft, wherein upon translation of the shaft from the second position back to the first position, the cinch cord is pulled proximally to cinch the open end of the bag closed. Further, a releasable latch may be configured to engage the proximal end of the cinch cord to the shaft, such that when the shaft is disposed in the first position, the releasable latch may be released to disengage the cinch cord from the shaft.

In some embodiments, the articulation mechanism includes an articulation wheel coupled to an articulation bar. The articulation wheel can be selectively rotatable about the longitudinal axis to longitudinally translate the articulation bar along the longitudinal axis. The articulation bar, in turn, can be configured to urge the end effector assembly to pivot relative to the shaft, thereby articulating the end effector assembly relative to the longitudinal axis.

In accordance with another aspect, a surgical retrieval apparatus is provided which includes a housing defining a longitudinal axis and having an elongated sleeve extending distally therefrom. The housing and the elongated sleeve cooperate to define a lumen extending longitudinally therethrough. A shaft having an end effector assembly disposed at a distal end thereof is selectively translatable through the lumen between a first position, wherein the end effector assembly is disposed within the elongated sleeve, and a second position, wherein the end effector assembly extends distally from the elongated sleeve. An articulation mechanism is coupled to the end effector assembly. The articulation mechanism is transitionable from a disengaged state to an engaged state upon translation of the shaft from the first position to the second position. A specimen retrieval bag is supported by the end effector assembly.

In some embodiments, in the engaged state, rotation of the articulation mechanism articulates the end effector assembly relative to the longitudinal axis.

In some embodiments, the articulation mechanism includes an articulation wheel coupled to an articulation bar upon transitioning of the articulation mechanism to the engaged state. Accordingly, in such embodiments, in the engaged state, the articulation wheel may be selectively rotated to translate the articulation bar along the longitudinal axis, and as the articulation bar is translated along the longitudinal axis, the end effector assembly is urged to articulate, i.e., pivot, relative to the longitudinal axis.

A clutch can be provided coupled to the articulation wheel such that rotation of the articulation wheel effects longitudinal translation of the clutch. The clutch, in turn, can include an engagement arm configured to engage the articulation bar upon transition of the articulation mechanism to the engaged state. A collar can be provided to bias the engagement arm of the clutch into engagement with the articulation bar upon translation of the shaft from the first position to the second position, e.g., upon transition of the articulation mechanism from the disengaged state to the engaged state.

In some embodiments, a release trigger is provided. The release trigger can be configured, upon actuation, to permit manual translation of the shaft from the second position back to the first position. Further, the release trigger may be configured to transition the articulation mechanism to the disengaged state upon actuation thereof. The surgical retrieval apparatus may otherwise be configured according to any of the other embodiments discussed herein.

In accordance with another aspect of the present disclosure, a surgical retrieval apparatus is provided which includes a housing having an elongated sleeve and a lumen extending therethrough. A shaft including an end effector assembly disposed at a distal end thereof is translatable between a first position, wherein the end effector assembly is disposed within the elongated sleeve, and a second position, wherein the end effector assembly extends distally from the elongated sleeve. A releasable latch is coupled to the shaft and is transitionable between an open condition and a closed condition. A specimen retrieval bag is releasably disposed on the end effector assembly and includes a cinch cord coupled to an open end thereof. The cinch cord extends proximally from the specimen retrieval bag to be engaged within the releasable latch. When the shaft is disposed in the first position, the releasable latch is operable, e.g. exposed from the housing, permitting manual manipulation of the releasable latch to release the cinch cord e.g., the latch can move between the open condition and the closed condition. When the shaft is disposed in the second position, the releasable latch is inoperable, e.g. positioned within the housing, inhibiting manual manipulation of the releasable latch, e.g., inhibiting access to the releasable latch. The surgical retrieval apparatus may otherwise be configured similarly to any of the other embodiments discussed herein.

In some embodiments, the releasable latch is retained in the closed condition via a protrusion-aperture engagement.

In another aspect, a surgical retrieval apparatus is provided which includes a housing having an elongated sleeve extending therefrom. A lumen extends through the housing and elongated sleeve. A shaft having an end effector assembly disposed at a distal end thereof is translatable between a first position and a second position. A plunger is slidably coupled to a proximal end of the shaft. The plunger is transitionable between a first condition, wherein the plunger is substantially disposed within the shaft, and a second condition, wherein the plunger substantially extends proximally from the shaft. A release trigger disposed on the housing is selectively actuatable to transition the plunger from the first condition to the second condition to facilitate translation of the shaft from the second position back to the first position.

In some embodiments, transitioning the plunger from the first condition to the second condition is inhibited when the shaft is disposed in the first position.

In some embodiments, when the shaft is disposed in the second position and the plunger is disposed in the first condition, the plunger is substantially flush with the housing, while when the shaft is disposed in the second position and the plunger is disposed in the second condition, the plunger extends proximally from the housing.

In some embodiments, upon actuation of the release trigger, a distal finger of the plunger is disengaged from an aperture defined within the shaft permitting the plunger to transition to the second condition. The surgical retrieval apparatus may otherwise be configured according to any of the other embodiments discussed herein.

A method of specimen retrieval is also provided in accordance with another aspect of the present disclosure. The method includes providing a surgical retrieval apparatus according to any of the embodiments discussed above. The method further includes inserting the shaft partially into the lumen through a proximal end of the housing to the first position, inserting the surgical retrieval apparatus through an opening in tissue, translating the shaft distally through the lumen to the second position, and articulating the end effector assembly with respect to the longitudinal axis to position an open end of the specimen retrieval bag adjacent the specimen of tissue to be retrieved.

In some embodiments, the method further includes translating the shaft proximally from the second position back to the first position such that the end effector assembly is once again disposed within the lumen.

In some embodiments, the method further includes locking the shaft in the first position and/or the second position. In such embodiments, a release trigger may be actuated to release, or unlock, the shaft to permit manual translation of the shaft between the first and second positions.

In some embodiments, the method further includes disengaging the proximal end of the cinch cord from the shaft upon movement of the shaft from second position back to the first position.

In some embodiments, the method further includes selectively rotating an articulation wheel about the longitudinal axis to articulate the end effector assembly relative to the longitudinal axis.

BRIEF DESCRIPTION OF THE DRAWINGS

Various embodiments of the subject surgical retrieval apparatus are described herein with reference to the drawings wherein.

DETAILED DESCRIPTION

Figure 1:
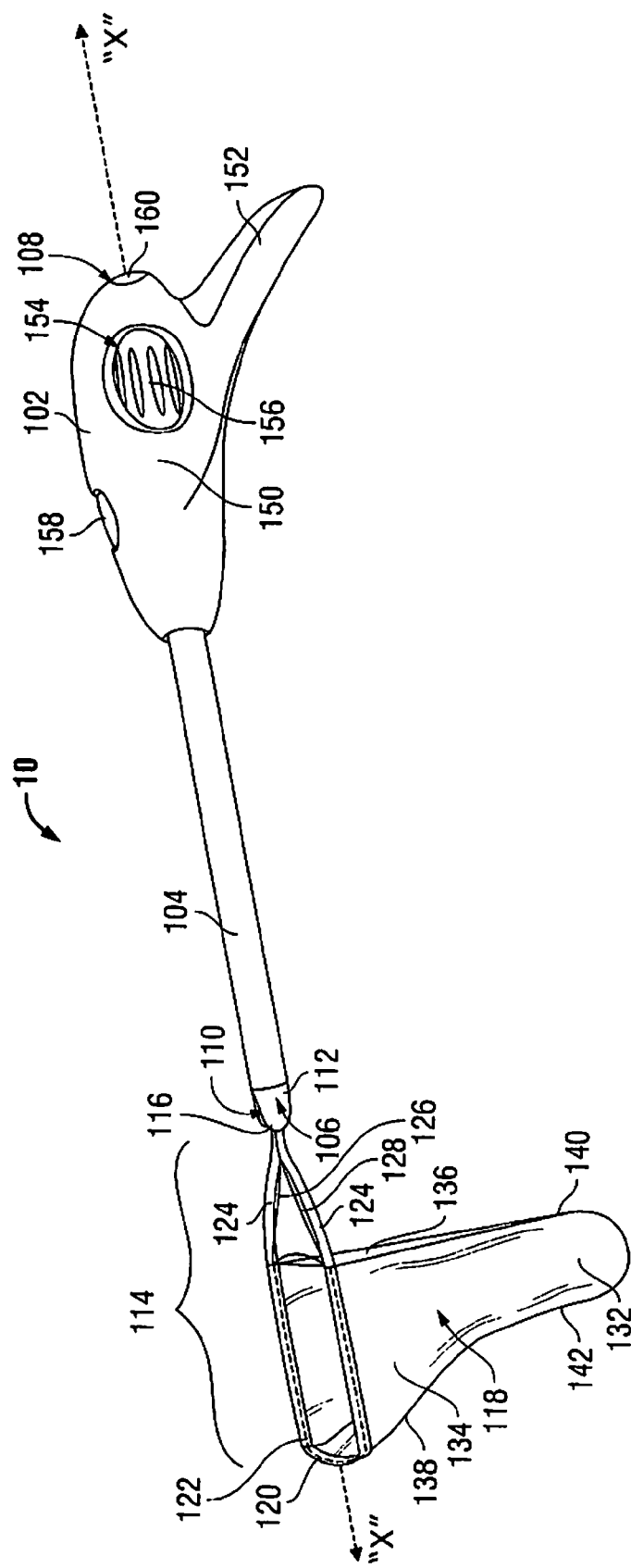
FIG. 1 is a side, perspective view of one embodiment of a surgical retrieval apparatus in accordance with the present disclosure.

Various embodiments of the presently disclosed surgical retrieval apparatus, and methods of using the same, will now be described in detail with reference to the drawings wherein like references numerals identify similar or identical elements. In the drawings, and in the following description, the term "proximal" should be understood as referring to the end of the apparatus, or component thereof, that is closer to the clinician during proper use, while the term "distal" should be understood as referring to the end that is farther from the clinician, as is traditional and conventional in the art.

Although the presently disclosed surgical retrieval apparatus is discussed with respect to minimally invasive thoracic procedures, it is within the scope of the present disclosure that the surgical retrieval apparatus is readily adaptable for use in other minimally invasive surgical procedures, including for example laparoscopic procedures.

Figure 2:
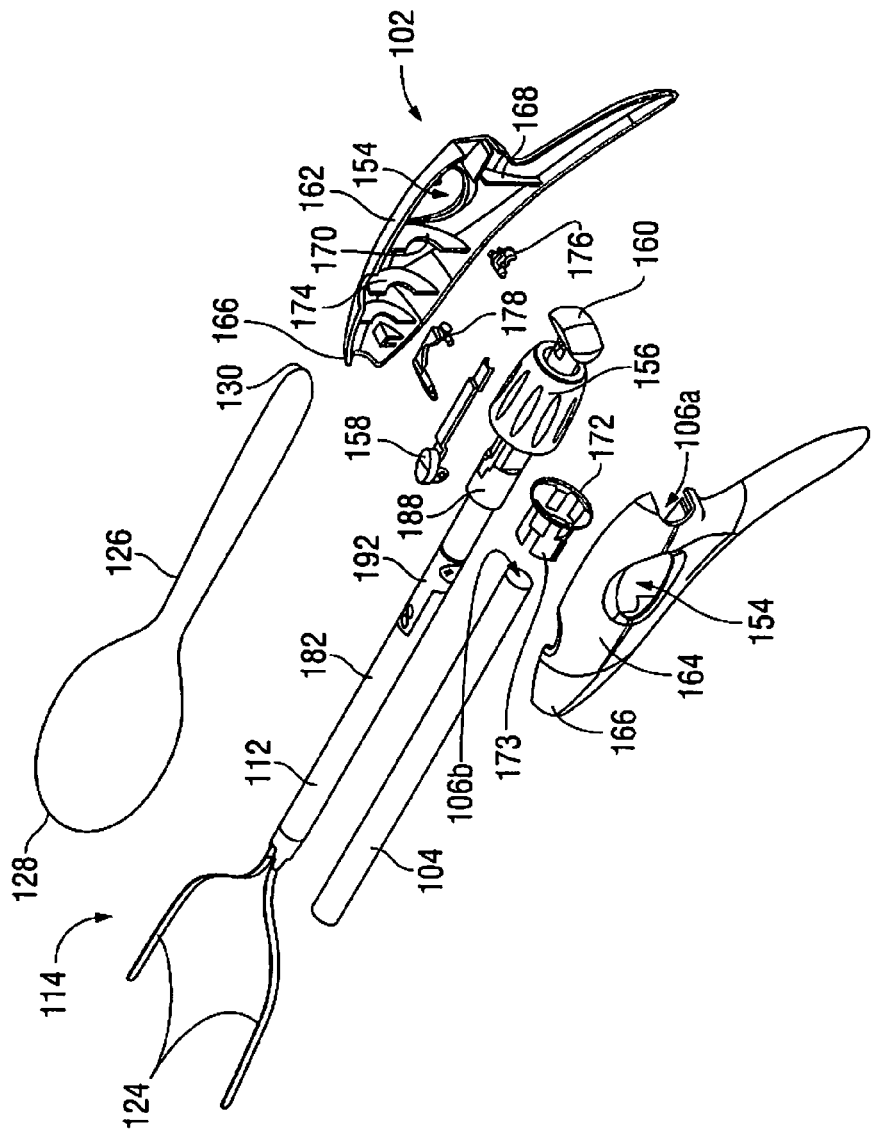
FIG. 2 is an exploded, perspective view of a housing of the surgical retrieval apparatus of FIG. 1.

Turning now to FIGS. 1 and 2, a surgical retrieval apparatus in accordance with the present disclosure is shown generally identified by reference numeral 10. Surgical retrieval apparatus 10 includes a housing 102 defining a longitudinal axis "X-X" and an elongated sleeve 104 extending distally from housing 102. Housing 102 defines a longitudinal passageway 106a extending therethrough, while elongated sleeve 104 defines a lumen 106b extending longitudinally therethrough. Passageway 106a and lumen 106b cooperate to define a channel 106 disposed about longitudinal axis "X-X" and extending distally from proximal aperture 108 of housing 102, through housing 102, through elongated sleeve 104, and through distal aperture 110 of elongated sleeve 104, i.e., channel 106 extends completely through surgical retrieval apparatus 10. A shaft 112 including an end effector assembly 114 pivotably coupled thereto at a distal end 116 thereof is slidably positionable within channel 106. More particularly, as will be described in greater detail below, shaft 112 is longitudinally translatable between a first, or insertion (and removal) position, wherein shaft 112 is inserted partially through proximal aperture 108 into channel 106 such that end effector assembly 114 is disposed within channel 106, and a second, or extended position, wherein shaft 112 is translated further distally through channel 106 such that end effector assembly 114 extends distally from distal aperture 110 of elongated sleeve 104.

With continued reference to FIG. 1, a specimen retrieval bag 118 is removably coupled to end effector assembly 114 and depends therefrom. More specifically, as shown in FIG. 1, specimen retrieval bag 118 is folded over at an open end 120 thereof to form a loop 122 around the outer periphery thereof. End effector assembly 114 includes a pair of arms 124 configured for positioning within loop 122 formed at open end 120 of specimen retrieval bag 118 to retain specimen retrieval bag 118 thereon. In the extended position, as shown in FIG. 1, arms 124 of end effector assembly 114 define a spaced-apart, curvate configuration for retaining specimen retrieval bag 118 thereon in an open condition, although other configurations are also contemplated, e.g., end effector assembly 114 may include linear arms 124. Further, as will be described in greater detail below, a cinch cord 126 is disposed through loop 122 of specimen retrieval bag 118 at a first end 128 thereof and is engaged to shaft 112 at a second end 130 (FIG.

21) thereof, such that, upon proximal translation of shaft 112 relative to specimen retrieval bag 118, open end 120 of specimen retrieval bag 118 is cinched closed.

It is envisioned that specimen retrieval bag 118 be formed from any suitable bio-compatible material (or materials), e.g., 30 Denier Ripstop Nylon, configured to retain a specimen of tissue "S" (FIGS. 7-9) therein and to inhibit the passage of fluids and biological materials therethrough. The bag can include a coating, such as a polyurethane coating, to prevent egress of fluid if a permeable bag is utilized or to improve the impermeability. The coating can be placed on the inner surface and/or the outer surface of the bag. As shown in FIG. 1, specimen retrieval bag 118 includes a lower portion 132 having a minimized cross-section configured to re-orient or re-position the specimen of tissue "S" (FIGS. 7-9) within specimen retrieval bag 118 to facilitate removal of specimen retrieval bag 118 from an internal body cavity, and a relatively expansive upper portion 134 configured to facilitate positioning of relatively large specimen of tissue "S" (FIGS. 7-9) within specimen retrieval bag 118. In other words, lower portion 132 has a smaller transverse dimension than the transverse dimension of upper portion 134. More specifically, upper portion 134 of specimen retrieval bag 118 has a first side 136 and an angled side 138 disposed opposite first side 136. Angled side 138 tapers inwardly such that the transverse dimension of upper portion 134 of specimen retrieval bag 118 progressively decreases toward the lower portion 132 of specimen retrieval bag 118. Wall 140, which opposes wall 142 in lower portion 132 of specimen retrieval bag 118, extends substantially parallel to wall 142 such that the transverse dimension of lower portion 132 remains substantially constant along a length thereof until transitioning at the curved walls in the lowermost portion. Alternatively, specimen retrieval bag 118 may be formed in various other configurations depending on the intended use of specimen retrieval bag 118. Other retrieval bag configurations are also contemplated such as those disclosed in U.S. application Ser. No. 61/389,391, filed Oct. 4, 2010, and application Ser. No. 61/430,206, filed Jan. 6, 2011, the entire contents of both these applications incorporated herein by reference.

Specimen retrieval bag 118 may in some embodiments further include a high-friction mesh material disposed on an inner surface thereof to facilitate retention of the tissue specimen "S" therein. In other embodiments, the bag shape is relied on to retain the specimen and a smooth inner surface is provided to enable easy passage of the tissue specimen from the upper loading area of the bag to the lower shaping region of the bag during extraction.

Additionally, in preferred embodiments, specimen retrieval bag 118 may include a channel (not explicitly shown) formed integral with or separately attached to specimen retrieval bag 118, e.g. attached to an inner surface thereof such as that disclosed in provisional patent application Ser. No. 61/389,391, filed Oct. 4, 2010, provisional application Ser. No. 61/430,206, filed Jan. 6, 2011, and provisional application Ser. No. 61/499,923, filed Jun. 22, 2011, the entire contents of each of these applications incorporated herein by reference. The channel may include at least one opening or slot along its length to allow the passage of fluids, e.g., air, into the channel. Further, a support member (or support members) (not shown) may be disposed within specimen retrieval bag 118 to help inhibit collapse of the channel and/or for biasing specimen retrieval bag 118 toward an open position upon deployment from surgical retrieval apparatus 10. The support member may be formed from, for example, an open cell material such as open cell foam, or other suitable material that enables the passage of air and/or fluid therethrough, thus allowing air and/or fluid to escape the lower portion of specimen retrieval bag 118 upon collapse or compression of specimen retrieval bag 118 to reduce the internal pressure within specimen retrieval bag 118.

Referring again to FIGS. 1-2, elongated sleeve 104 is configured for insertion through an opening in tissue, e.g., through a thoracic surgical access port (not shown) disposed within an incision in tissue between adjacent ribs of a patient. As such, it is envisioned that elongated sleeve 104 defines a sufficient length such that elongated sleeve 104 may be advanced into the thoracic cavity to a position adjacent a tissue specimen "S" (FIGS. 7-9) to be removed, while housing 102 remains external of the patient. Further, it is envisioned that elongated sleeve 104 defines a diameter sufficiently large to permit passage of end effector assembly 114 and shaft 112 therethrough, but sufficiently small such that elongated sleeve 104 may be inserted between adjacent ribs of a patient, e.g., through a thoracic access port (not shown) disposed within an incision and intercostal space therebetween.

Housing 102, as shown in FIGS. 1 and 2, includes a body portion 150 and a handle portion or gripping portion 152. Body portion 150 of housing 102 includes a proximal aperture 108, as mentioned above, that is configured to receive shaft 112 therethrough. Body portion 150 of housing 102 also includes a pair of oval-shaped windows 154 (although other configurations are contemplated). Windows 154 permit the clinician to grasp and manipulate articulation wheel 156 for articulating end effector assembly 114 relative to longitudinal axis "X-X" as described below. Surgical retrieval apparatus 10 further includes a release trigger 158 coupled to body portion 150 of housing 102. As will be described in greater detail below, release trigger 158 is operable to release plunger 160, which is releasably engageable with shaft 112. When released, plunger 160 extends proximally from proximal aperture 108 of body portion 150 of housing 102, allowing the clinician to grasp plunger 160 and pull proximally to translate shaft 112 proximally back to the insertion (retracted) position. As shaft 112 is translated back to the insertion position, end effector assembly 114 is translated proximally back within elongated sleeve 104.

Continuing with reference to FIGS. 1-2, handle portion 152 of housing 102 extends downwardly and proximally from body portion 150 to define an ergonomically-enhanced configuration of housing 102 for grasping by the clinician. More specifically, the configuration of handle portion 152 of housing 102 permits the clinician to grasp housing 102 in numerous configurations, while still being able to firmly grasp and fully manipulate and operate surgical retrieval apparatus 10. For example, the clinician may grasp housing 102 using a pistol grip, a palm grip, an upside-down grip, a rear grip, a front grip, etc. The specific grip used may depend on the clinician's preference or the surgical procedure being performed.

Figure 3:
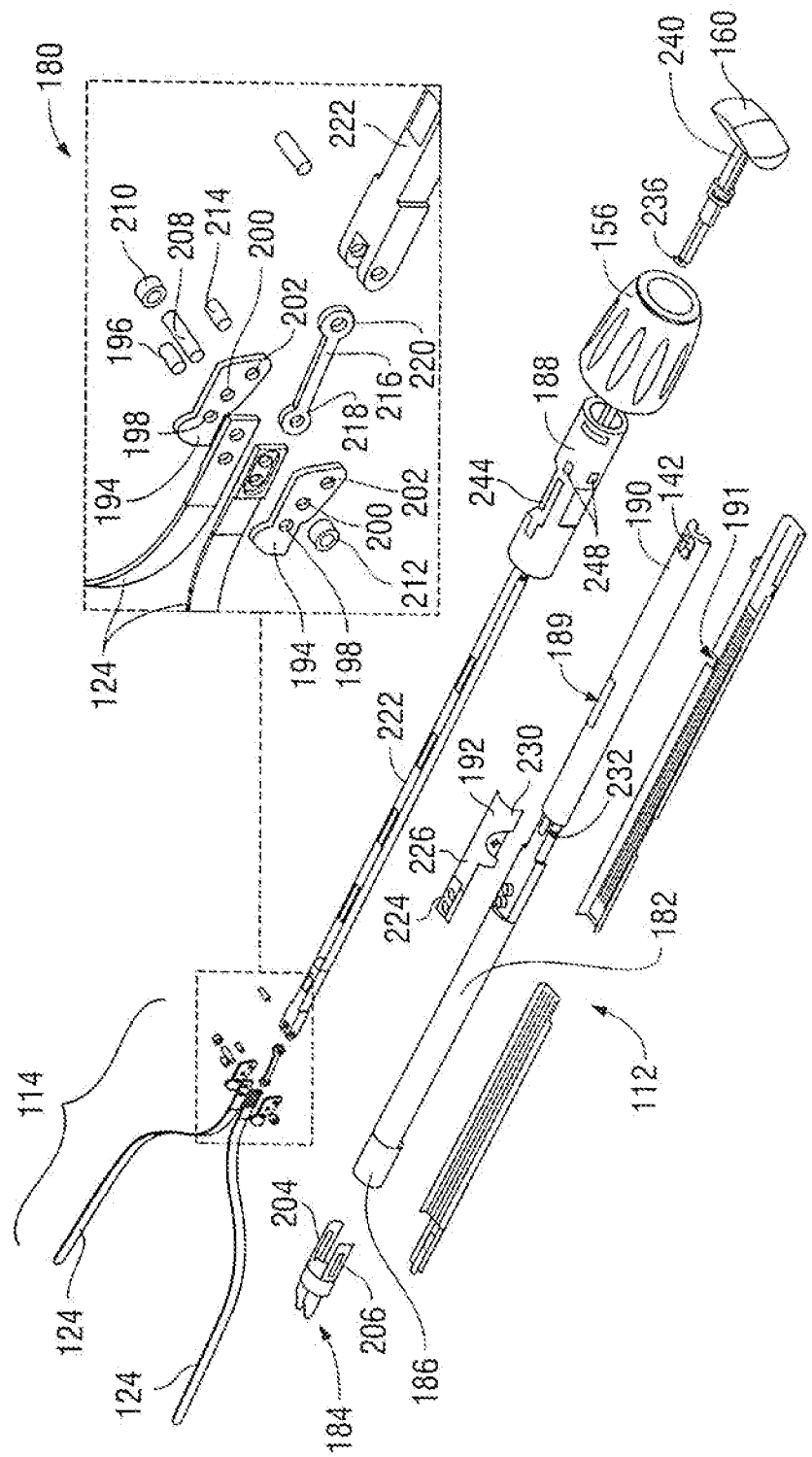
FIG. 3 is an exploded, perspective view of a shaft and end effector assembly of the surgical retrieval apparatus of FIG. 1.

Turning now to FIGS. 2-3, the internal components of surgical retrieval apparatus 10 will be described. As shown in FIG. 2, housing 102 includes a pair of housing parts 162, 164 that cooperate to form housing 102. Housing parts 162, 164 also define passageway 106a extending through housing 102, which forms a portion of channel 106. Elongated sleeve 104 is fixedly engaged within distal end 166 of body portion 150 of housing 102 and extends distally therefrom along longitudinal axis "X-X" defining lumen 106b therethrough. As mentioned above, lumen 106b cooperates with passageway 106a of housing 102 to form channel 106 extending through surgical retrieval apparatus 10 to permit translation of shaft 112 therethrough. As mentioned above, windows 154 defined within housing parts 162, 164 of housing 102 provide access to articulation wheel 156, which is rotatably disposed within housing 102 adjacent windows 154. Articulation wheel 156 is longitudinally maintained in position within housing 102 via a pair of retainer walls 168 and 170. A collar 172 is positioned adjacent to and distal of articulation wheel 156 and is likewise retained in longitudinal position via a pair of retainer walls 170, 174. A clutch 188 disposed about longitudinal axis "X-X" and slidably positioned within collar 172 is coupled to articulation wheel 156. As will be described in greater detail below, collar 172 selectively engages clutch 188 with articulation mechanism 180 (FIGS. 12-15) to permit articulation of end effector assembly 114 via rotation of articulation wheel 156.

As best shown in FIG. 2, housing 102 further includes a shaft lock 176 pivotably coupled thereto and configured to retain shaft 112 in position once inserted into channel 106, e.g., shaft lock 176 is configured to retain shaft 112 in the first and/or second positions. Housing 102 also includes a release trigger 158 coupled thereto, as mentioned above. Release trigger 158, in turn, is coupled to a lever 178 that, upon actuation of release trigger 158, decouples plunger 160 from shaft 112, allowing plunger 160 to automatically extend proximally, e.g., "pop-out," from shaft 112. Release trigger 158, upon actuation, also rotates collar 172 about longitudinal axis "X-X" relative to clutch 188 to disengage the articulation mechanism 180 (FIGS. 12-15), e.g., to inhibit articulation of end effector assembly 114 via rotation of articulation wheel 156.

With reference now to FIG. 3, shaft 112, as mentioned above, is slidably positioned within channel 106 (FIG. 1) of housing 102 and elongated sleeve 104. Shaft 112 includes a tubular member 182, a nose 184 disposed at a distal end 186 of tubular member 182, a releasable latch 192 disposed on an outer surface of tubular member 182, and an articulation mechanism 180 positioned within tubular member 182 and longitudinally translatable with respect to tubular member 182. Tubular member 182 further includes an elongated slot 189 (or a pair of opposed elongated slots 189) defined therethrough toward a proximal end 190 thereof. Plunger 160 is releasably engageable within tubular member 182 at proximal end 190 thereof.

Nose 184, as shown in FIGS. 2-3, is fixedly engaged to distal end 186 of tubular member 182 and includes end effector assembly 114 extending distally therefrom. More particularly, arms 124 of end effector assembly 114 are coupled to rotatable plates 194 disposed on either side of arms 124 via a first pin 196. Rotatable plates 194 each include a distal aperture 198 for securing pins 196 therethrough, a central aperture 200, and a proximal aperture 202 disposed proximally of and offset below central aperture 200. Rotatable plates 194 are pivotably coupled to flanges 204, 206 of nose 184 via a second pivot pin 208 that extends through arms 124, central apertures 200 of rotatable plates 194, and flanges 204, 206, respectively. Washers 210, 212 provide spacing between rotatable plates 194 and flanges 204, 206 of nose 184 and maintain the relative lateral positioning of the above-mentioned components. A third pin, pivot pin 214, is disposed through proximal apertures 202 of rotatable plates 194 for pivotably coupling articulation linkage 216 to rotatable plates 194 and, thus, to arms 124, of end effector assembly 114. An overmolded assembly can be utilized as an alternative to the plated assembly.

With continued reference to FIG. 3, and as mentioned above, articulation mechanism 180 includes an articulation linkage 216 that is pivotably coupled to rotatable plates 194 and arms 124 of end effector assembly 114 at a first distal end 218 thereof. Articulation linkage 216 is pivotably coupled, at a second proximal end 220 thereof, to articulation bar 222 of articulation mechanism 180. As will be described in greater detail below, articulation bar 222 is longitudinally translatable through tubular member 182 upon rotation of articulation wheel 156 to urge articulation linkage 216 and, thus, pin 214 distally, thereby rotating rotatable plates 194 and arms 124 about pivot pin 208 to articulate arms 124 of end effector assembly 114 relative to longitudinal axis "X-X," e.g., off of longitudinal axis "X-X." On the other hand, when articulation wheel 156 is rotated in the opposite direction, articulation bar 222 is translated proximally, pulling articulation linkage 216 proximally and, as a result, rotating rotatable plates 194 and arms 124 about pivot pin 208 to articulate arms 124 of end effector assembly 114 in an opposite direction, e.g., back into alignment with longitudinal axis "X-X." Put more generally, upon rotation of articulation wheel 156 about longitudinal axis "X-X," articulation wheel 156, collar 172 (FIG. 2), and clutch 188 cooperate to translate the rotational motion of articulation wheel 156 into longitudinal motion of articulation bar 222 which, in turn, articulates end effector assembly 114 relative to longitudinal axis "X-X."

Such articulation provides increased flexibility in the placement of the retrieval bag within the body cavity, e.g. thoracic cavity. It also enables the retrieval bag to be placed away from the immediate space adjacent the main access incision and placed towards the apex of the cavity. This provides the surgeon with a functional space immediately below the incision where the specimen can be easily and directly manipulated and where the space can be visualized from the separate scope port. That is, the bag can be out of the way of loading and visualization.

Continuing with reference to FIG. 3, releasable latch 192, as mentioned above, is disposed on an outer surface of tubular member 182 at a proximal portion. More specifically, releasable latch 192 is snap-fit, or otherwise engaged to tubular member 182 at a first end 224 thereof and includes a flexible, or hinged body 226. A protrusion 228 (FIG. 21) extends downwardly from a second end 230 of releasable latch 192 and is configured to engage a corresponding aperture 232 defined within tubular member 182 in a friction-fit engagement (or other suitable engagement) therewith. Thus, as can be appreciated, the clinician may manipulate releasable latch 192 between a closed position, wherein protrusion 228 (FIG. 21) is engaged within aperture 232, and an open condition, wherein protrusion 228 (FIG. 21) is disengaged from aperture 232. In the open condition, second end 230 of releasable latch 192 is flexed, or hinged upwardly away from tubular member 182. As will be described in greater detail below, releasable latch 192 is configured to releasably retain cinch cord 126 of specimen retrieval bag 118 (FIG. 1) thereon.

Figure 4:
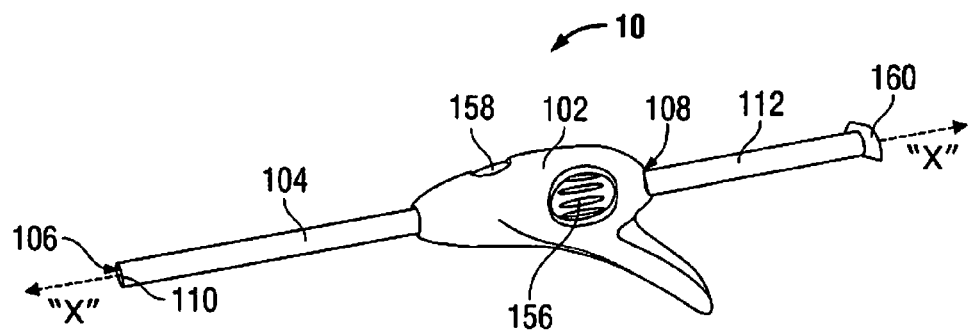
FIG. 4 is a side, perspective view of the surgical retrieval apparatus of FIG. 1 shown in an insertion position.

Turning now to FIGS. 4-9, the overall use and operation of surgical retrieval apparatus 10 will be described, with a more detailed description of the working components of surgical retrieval apparatus 10 being described thereafter with reference to FIGS. 2-3 and 10-21. Initially, specimen retrieval bag 118 is positioned on arms 124 of end effector assembly 114. In this position, cinch cord 126 is disposed through loop 122 of specimen retrieval bag 118 and extends proximally therefrom along shaft 112, wherein second end 130 of cinch cord 126 is retained within releasable latch 192. Specimen retrieval bag 118 is initially disposed in an undeployed, or collapsed condition, e.g., specimen retrieval bag 118 is rolled-up, to permit insertion of end effector assembly 114 and specimen retrieval bag 118 into elongated sleeve 104. In this initial insertion position, as shown in FIG. 4, shaft 112 extends proximally from housing 102 and partially through proximal aperture 108 of housing 102 and into channel 106 such that end effector assembly 114 is disposed and collapsed within elongated sleeve 104. Thus, in FIG. 4, shaft 112 is disposed in the insertion position. In this insertion position, since end effector assembly 114 does not extend from elongated sleeve 104, surgical retrieval apparatus 10 defines a reduced diameter to facilitate passage of elongated sleeve 104 through an incision in tissue, a natural body opening, or through an access port (not shown) (e.g. disposed between adjacent ribs of a patient) and into the internal surgical site. In other words, with surgical retrieval apparatus 10 disposed in the insertion position, surgical retrieval apparatus 10 may be inserted through an opening in tissue, e.g., through a thoracic access port (not shown).

Figure 5:
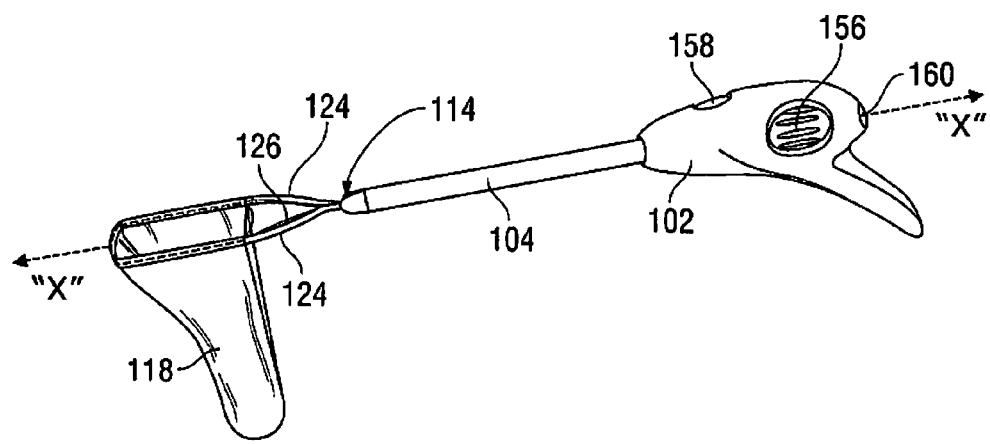
FIG. 5 is a side, perspective view of the surgical retrieval apparatus of FIG. 1 showing the end effector assembly in the deployed (extended) position.

Once surgical retrieval apparatus 10 has been inserted into an internal body cavity, e.g., the thoracic cavity, and positioned adjacent a tissue specimen "S" to be removed, shaft 112 is translated distally through channel 106 from the insertion position to the extended (deployed) position such that end effector assembly 114 is extended from elongated sleeve 104, i.e., to the second, or extended (deployed) position, to deploy specimen retrieval bag 118. More specifically, in order to deploy specimen retrieval bag 118, as shown in FIG. 5, the clinician grasps plunger 160 and advances plunger 160 distally, translating shaft 112 distally through channel 106. Shaft 112 is translated distally through channel 106 until end effector assembly 114 extends distally from elongated sleeve 104. In this position, plunger 160 is disposed within proximal aperture 108 of housing 102. That is, in this extended or deployed position, plunger 160 is substantially flush with housing 102 to enable the multiple of hand holds described herein. Also, being flush, the plunger 160 is inhibited from being caught on the clinician's clothing, other surgical instrumentation, etc., or from being inadvertently withdrawn from housing 102. As can be appreciated, as end effector assembly 114 emerges from elongated sleeve 104, arms 124 move to their normal expanded position to open specimen retrieval bag 118 and the specimen retrieval bag 118 is deployed, or unrolled, to an open condition, as shown in FIG. 5, e.g., due to the bias of specimen retrieval bag 118 toward the open condition.

Figure 6:
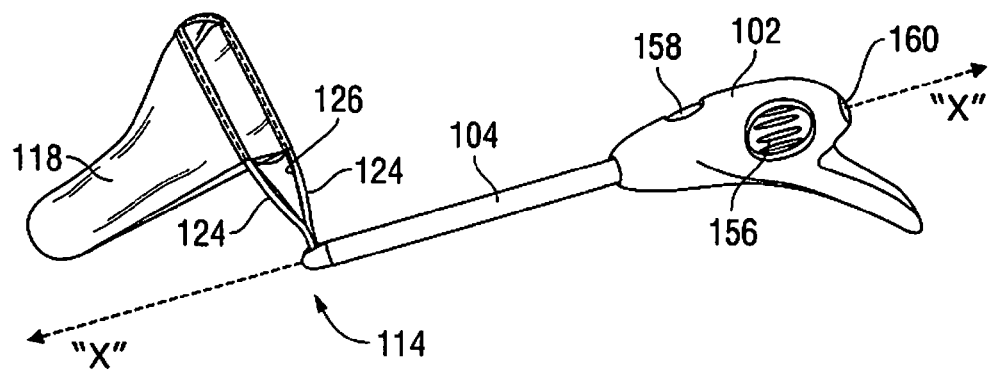
FIG. 6 is a side, perspective view of the surgical retrieval apparatus of FIG. 1 showing the end effector assembly articulated relative to the shaft.

Turning now to FIG. 6, with shaft 112 in the extended position, end effector assembly 114 may be articulated relative to longitudinal axis "X-X," e.g., via rotation of articulation wheel 156, and/or surgical retrieval apparatus 10 may be manipulated in order to better position specimen retrieval bag 118 relative to the tissue specimen "S" to be retrieved. Once in position, the tissue specimen "S" is moved into specimen retrieval bag 118, through open end 120 thereof, e.g., via use of a surgical grasper (not shown) or any other suitable mechanism which can be inserted through another access port.

Figure 7:
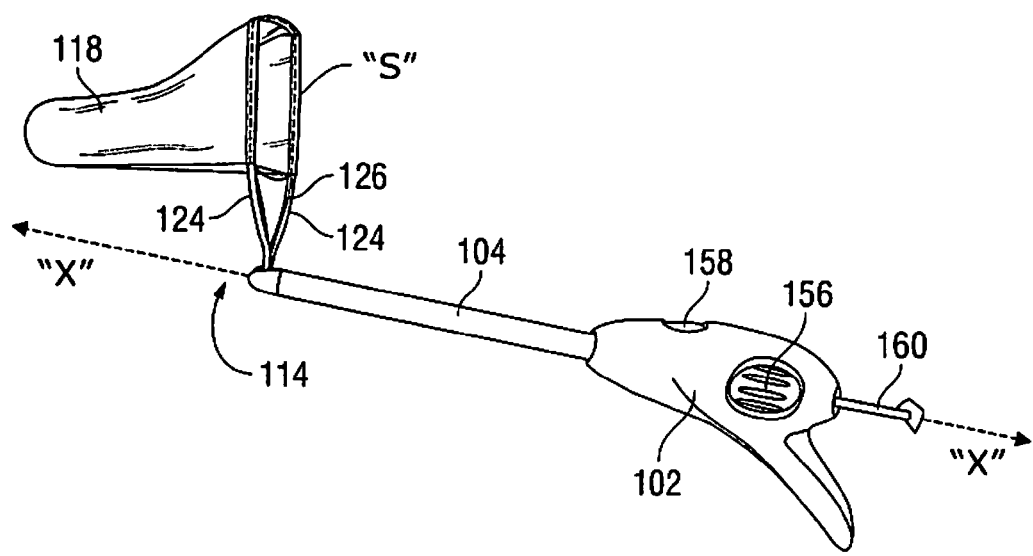
FIG. 7 is a side, perspective view of the surgical retrieval apparatus of FIG. 1, wherein a plunger has been released to permit retraction of the end effector assembly.
Figure 8:
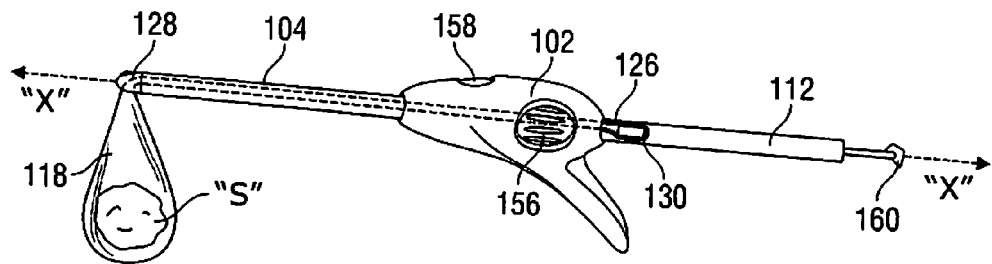
FIG. 8 is a side, perspective view of the surgical retrieval apparatus of FIG. 1, wherein the shaft and the end effector assembly have been returned to the insertion position to close the specimen retrieval bag.

With the tissue specimen "S" disposed within specimen retrieval bag 118, as shown in FIG. 7, end effector assembly 114 and shaft 112 are translated proximally relative to housing 102 back to the insertion (retracted) position to cinch-closed specimen retrieval bag 118 with the specimen of tissue "S" retained therein. In order to return shaft 112 to the insertion position, release trigger 158 is actuated to disengage articulation mechanism 180 (FIG. 12-15) and to extend plunger 160 proximally from housing 102. With release trigger 158 having been actuated to extend plunger 160, plunger 160 may be grasped by the clinician and translated proximally to return shaft 112 and end effector assembly 114 to the insertion position, as shown in FIG. 8. As shaft 112 is translated proximally back through channel 106, specimen retrieval bag 118 is inhibited from being translated through elongated sleeve 104 via interference member 234 (see FIG. 20) which has been advanced from sleeve 104 with the end effector assembly 114, and, thus, remains disposed adjacent distal aperture 110 of elongated sleeve 104. Accordingly, as shaft 112 is translated proximally back through channel 106, arms 124 of end effector assembly 114 are translated proximally relative to specimen retrieval bag 118, ultimately disengaging arms 124 from within loop 122 of specimen retrieval bag 118 and releasing specimen retrieval bag 118 from end effector assembly 114, as shown in FIG. 8. Further, since cinch cord 126 is engaged within releasable latch 192, the proximal translation of shaft 112 relative to specimen retrieval bag 118 pulls cinch cord 126 proximally relative to specimen retrieval bag 118, thereby cinching closed open end 120 of specimen retrieval bag 118 with the tissue specimen "S" retained therein.

Figure 9:
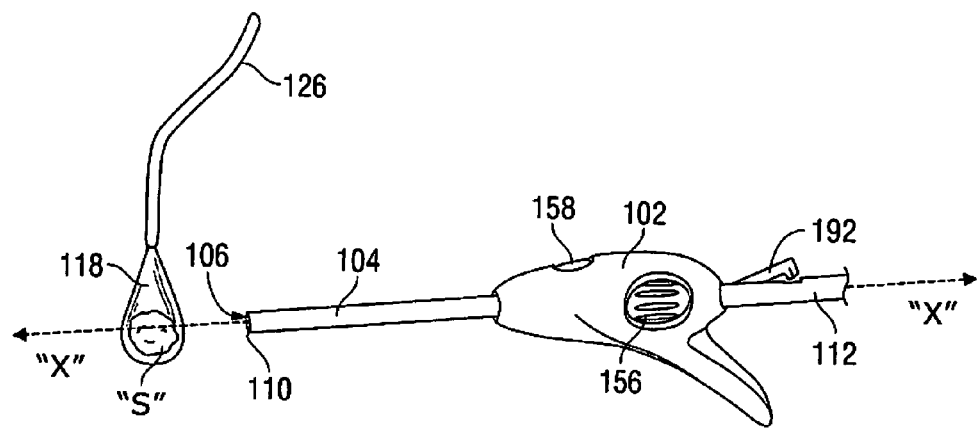
FIG. 9 is a side, perspective view of the surgical retrieval apparatus of FIG. 1 wherein the specimen retrieval bag has been released from the surgical retrieval apparatus.

Thereafter, as shown in FIG. 9, releasable latch 192 may be transitioned from the closed position to the open condition to release cinch cord 126, disengaging specimen retrieval bag 118 from surgical retrieval apparatus 10. Surgical retrieval apparatus 10 may then be withdrawn from the surgical site, e.g., the thoracic cavity, leaving specimen retrieval bag 118 behind. Next, specimen retrieval bag 118 may be removed from the thoracic cavity, e.g., via grasping second end 130 of cinch cord 126 with a suitable surgical instrument (not shown).

Figure 10:
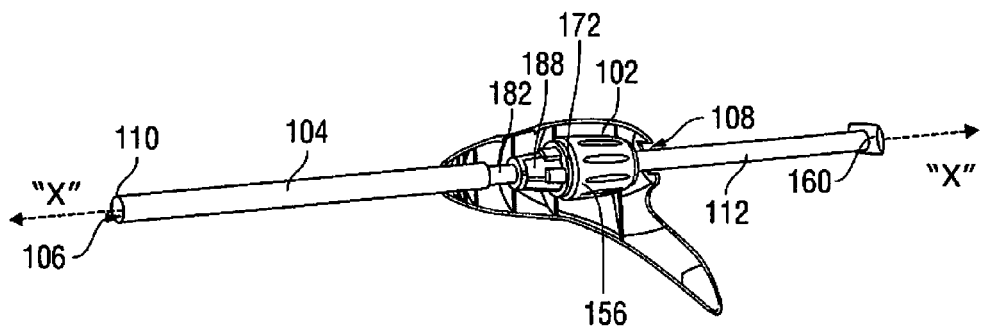
FIG. 10 is a side, cut-away view of the surgical retrieval apparatus of FIG. 1 shown in the insertion position, corresponding to the position of FIG. 4.

Referring now to FIG. 10, in conjunction with FIGS. 2-3, surgical retrieval apparatus 10 is shown in the insertion (and removal) position. As mentioned above, in the insertion position, shaft 112 extends partially through proximal aperture 108 of housing 102 into channel 106. More specifically, shaft 112 extends only partially through channel 106 such that end effector assembly 114 is disposed within elongated sleeve 104, but does not extend distally therefrom. As such, a portion of shaft 112, including releasable latch 192 and plunger 160, remains proximal of channel 106, i.e., a portion of shaft 112 extends proximally from housing 102.

In the insertion position, clutch 188 is disengaged from articulation bar 222, which is disposed within tubular member 182 of shaft 112. More particularly, in the insertion position, clutch 188 is spaced-apart from elongated slot 189 of tubular member 182 such that clutch 188 cannot extend into tubular member 182 to engage articulation bar 222. Accordingly, in the insertion position, articulation of end effector assembly 114 via rotation of articulation wheel 156 is inhibited.

Further, in this insertion position, a distal finger 236 of plunger 160 is engaged within aperture 191 defined within tubular member 182 to engage plunger 160 to tubular member 182 of shaft 112 such that proximal end 240 of plunger 160 abuts proximal end 190 of tubular member 182 of shaft 112. Lever 178 of release trigger 158, on the other hand, is spaced-apart relative to aperture 191 of tubular member 182 and, thus, tubular member 182 inhibits, or locks-out release trigger 158 from being actuated.

Figure 11:
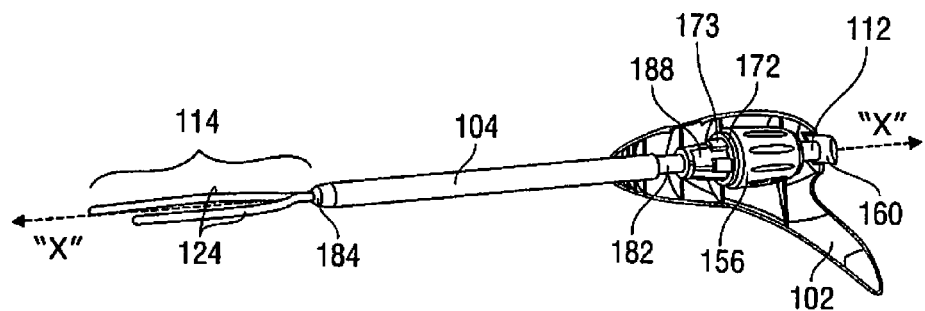
FIG. 11 is a side, cut-away view of the surgical retrieval apparatus of FIG. 1 shown with the end effector assembly in the deployed (extended) position, corresponding to the position of FIG. 5 (the retrieval bag removed for clarity)
Figure 12:
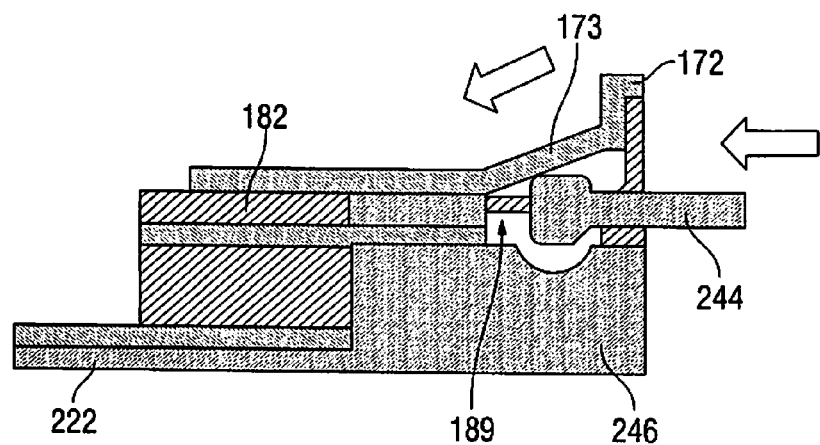
FIG. 12 is an enlarged, longitudinal, cross-sectional view of an articulation assembly of the surgical retrieval apparatus of FIG. 1 wherein the articulation assembly is disposed in an engaged position.
Figure 13:
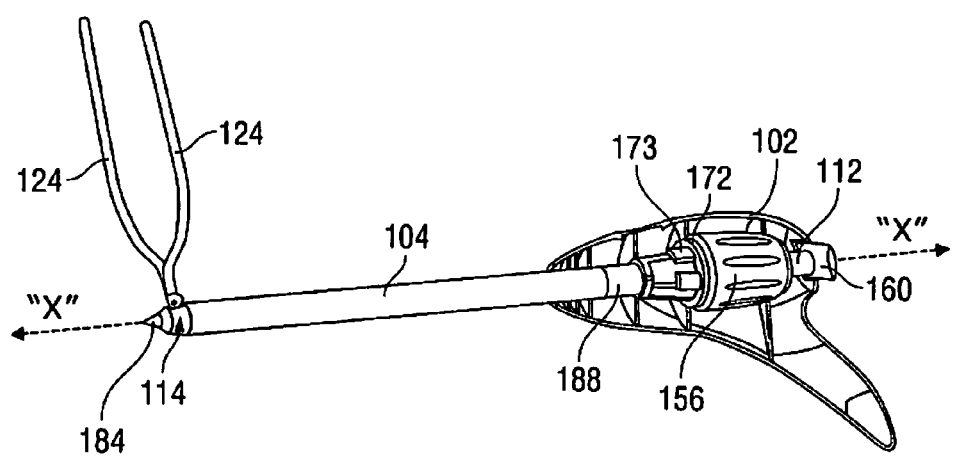
FIG. 13 is a side, cut-away view of the surgical retrieval apparatus of FIG. 1 shown with the end effector assembly articulated relative to the shaft, corresponding to the position of FIG. 6 (the retrieval bag removed for clarity)
Figure 14:
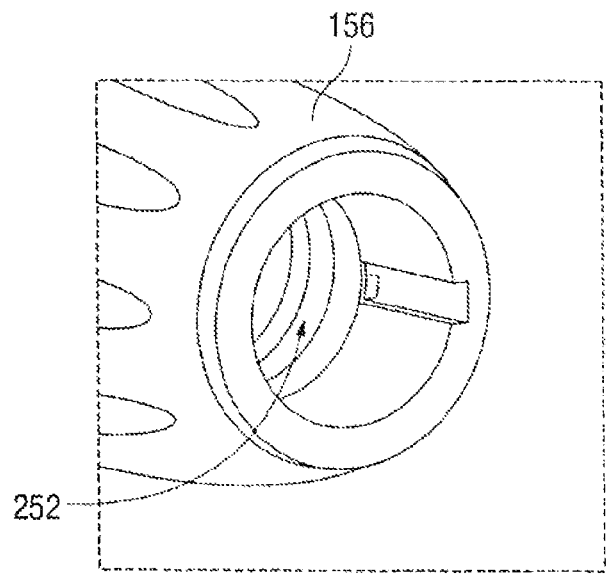
FIG. 14 is an isolated, rear, perspective view of an articulation wheel of the articulation assembly of the surgical retrieval apparatus of FIG. 1.

Turning now to FIG. 11, in conjunction with FIGS. 2-3, surgical retrieval apparatus 10 is shown in the extended or deployed position. As mentioned above, to transition surgical retrieval apparatus 10 from the insertion position to the extended position, the clinician, while grasping housing 102, advances shaft 112 distally through channel 106 until end effector assembly 114 extends distally from elongated sleeve 104, e.g., the extended (deployed) position. As shaft 112 is advanced distally through channel 106, shaft lock 176 is pivoted relative to housing 102 into engagement with proximal slot 142 defined within tubular member 182 of shaft 112 as proximal slot 142 is translated into position adjacent shaft lock 176. As can be appreciated, shaft lock 176 retains shaft 112 in the extended position (see FIG. 16), inhibiting inadvertent translation of shaft 112 from the extended position. Further, shaft lock 176 may be biased downwardly such that shaft lock 176 is automatically urged into engagement with proximal slot 142 upon positioning of proximal slot 142 adjacent shaft lock 176, e.g., upon translation of shaft 112 to the extended position. Additionally, in the extended position, aperture 191 of tubular member 182 is positioned adjacent lever 178 of release trigger 158 such that release trigger 158 is no longer locked-out. As such, release trigger 158 may thereafter be actuated to release plunger 160, allowing the clinician to return shaft 112 to the insertion (and removal) position at the completion of the procedure.

With reference now to FIGS. 12-15, in conjunction with FIG. 3, upon translation of shaft 112 to the extended position, collar 172 urges articulation arm 244 of clutch 188 through elongated slot 189 of tubular member 182 and into engagement with proximal hub 246 of articulation bar 222, e.g., via a protrusion-aperture engagement, to engage articulation mechanism 180. More specifically, as shaft 112 is translated to the extended position, elongated slot 189 is moved into alignment with articulation arm 244 of clutch 188, allowing flange 173 of collar 172 to urge articulation arm 244 inwardly into engagement with proximal hub 246 of articulation bar 222. Although only one elongated slot 189 of tubular member 182, one articulation arm 244 of clutch 188, and one flange 173 of collar 172 are shown in the Figures, it is envisioned that a second elongated slot (not shown), articulation arm (not shown), and flange (not shown), respectively, may similarly be disposed opposite the first, such that the articulation arms 244 are urged into engagement with articulation bar 222 via flanges 173 of collar 172 on opposing side thereof.

Further, radial tabs 248 disposed on an outer periphery of clutch 188 are engaged within helical threading 252 disposed on the interior surface of articulation wheel 156. Helical threading 252 of articulation wheel 156 is pitched such that, upon rotation of articulation wheel 156 in a first direction, clutch 188 is translated distally along longitudinal axis "X-X" relative to shaft 112 due to the engagement of tabs 248 within threading 252. As can be appreciated, rotation of articulation wheel 156 in the opposite direction translates clutch 188 proximally along longitudinal axis "X-X" relative to shaft 112.

Figure 15:
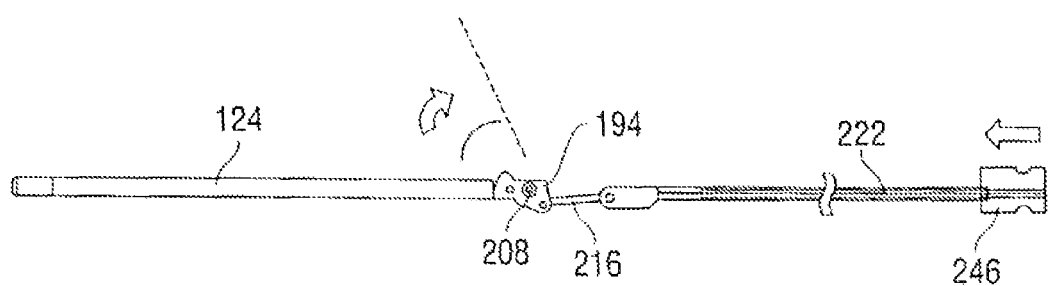
FIG. 15 is an isolated, side view of an articulation bar of the articulation assembly of the surgical retrieval apparatus of FIG. 1 shown pivotably engaged to the end effector assembly.

Continuing with reference to FIGS. 12-15, distal translation of clutch 188, e.g., upon rotation of articulation wheel 156, translates articulation arm 244 of clutch 188 distally which, in turn, urges articulation bar 222 distally (due to the protrusion-aperture engagement therebetween). As articulation bar 222 is urged distally, as best shown in FIG. 15, articulation linkage 216 is likewise translated distally to urge rotatable plates 194 to pivot about pivot pins 208 disposed through central apertures 200 thereof. Accordingly, since arms 124 of end effector assembly 114 are fixedly engaged with rotatable plates 194, arms 124 are also pivoted, or articulated relative to longitudinal axis "X-X," e.g., to the position shown in FIG. 13. As can be appreciated, arms 124 of end effector assembly 114 may be articulated to the desired position to facilitate positioning of the tissue specimen "S" within specimen retrieval bag 118. Articulation wheel 156 may also be rotated in an opposite direction to translate articulation bar 222 proximally. As described above, upon proximal translation of articulation bar 22, rotatable plates 194 are pulled to rotate such that end effector assembly 114 is articulated back toward longitudinal axis "X-X".

Figure 16:
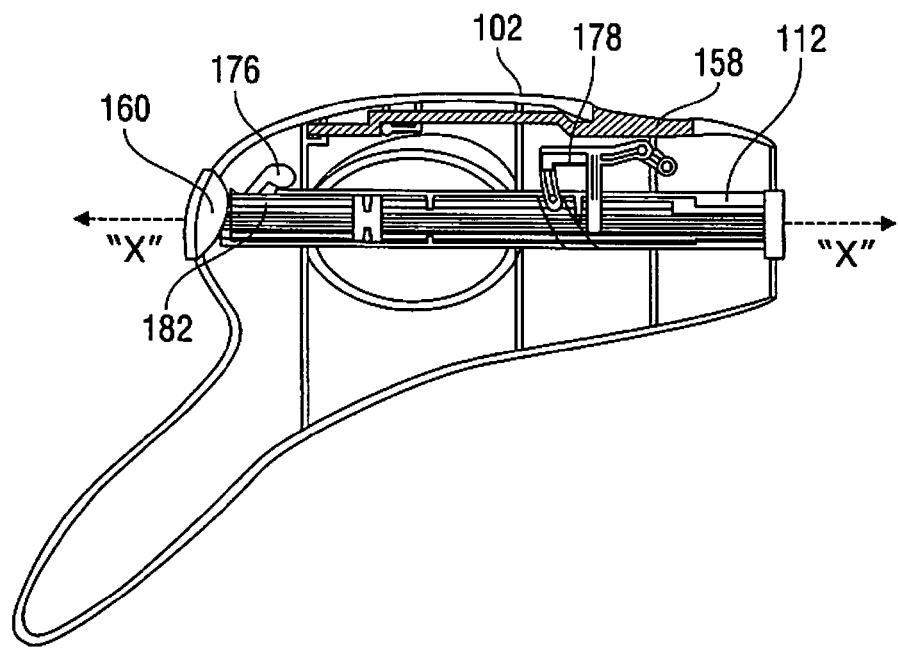
FIG. 16 is a longitudinal, cross-sectional view of the housing of the surgical retrieval apparatus of FIG. 1 shown in the deployed position.
Figure 17:
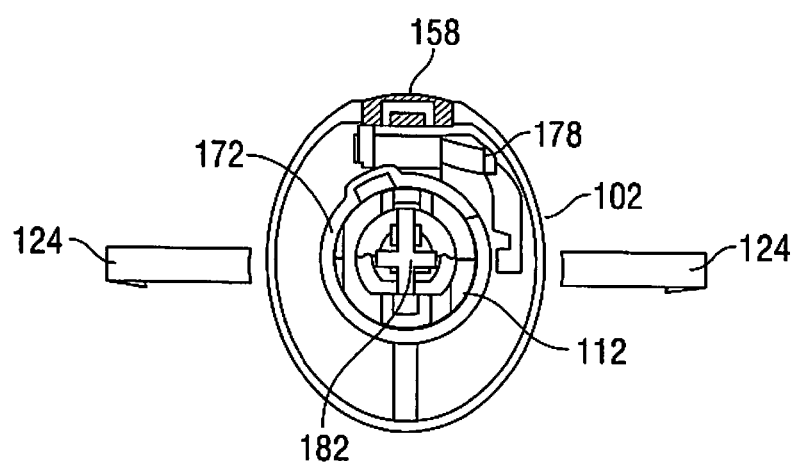
FIG. 17 is a transverse, cross-sectional view of the housing of surgical retrieval apparatus of FIG. 1 shown in the deployed position.

Referring now to FIGS. 16-17, in conjunction with FIGS. 2-3, housing 102 of surgical retrieval apparatus 10 is shown wherein shaft 112 is disposed in the extended position, release trigger 158 and lever 178 are in un-actuated or initial positions, and shaft lock 176 is engaged with tubular member 182 of shaft 112 to retain shaft 112 in the extended position. As described above, in this extended position, the clinician may articulate end effector assembly 114 or otherwise manipulate surgical retrieval apparatus 10 for positioning the tissue specimen "S" within specimen retrieval bag 118 (see FIGS. 4-9). Once the tissue specimen "S" is disposed within specimen retrieval bag 118, specimen retrieval bag 118 may be cinched closed, released from surgical retrieval apparatus 10 and, ultimately removed from the thoracic cavity (see FIGS. 4-9).

Figure 18:
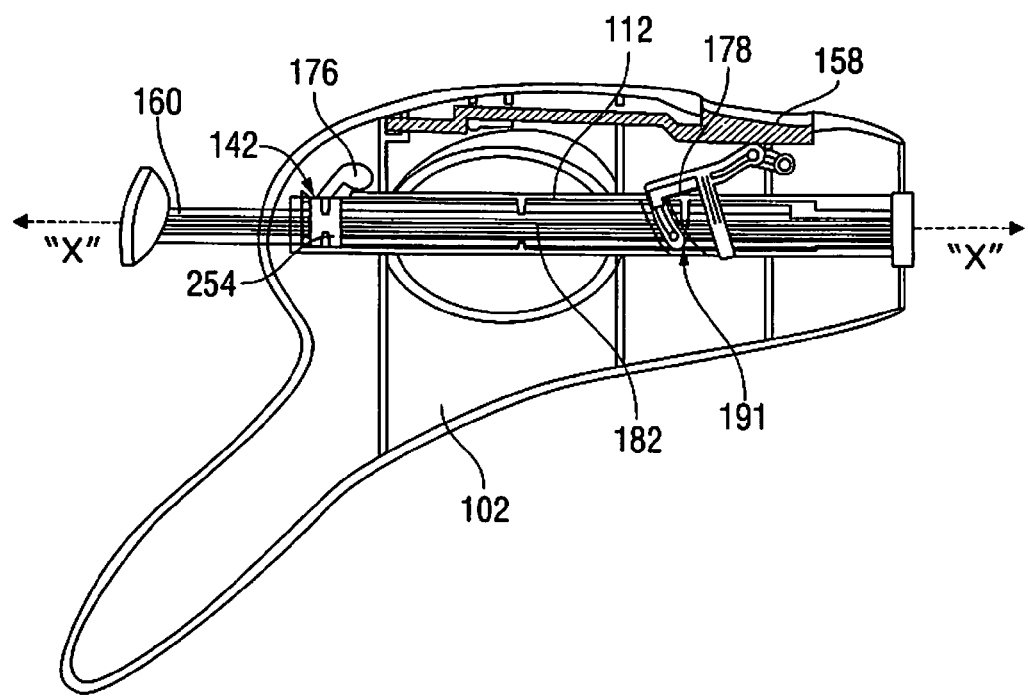
FIG. 18 is a longitudinal, cross-sectional view of the housing of the surgical retrieval apparatus of FIG. 1 wherein the plunger has been released.
Figure 19:
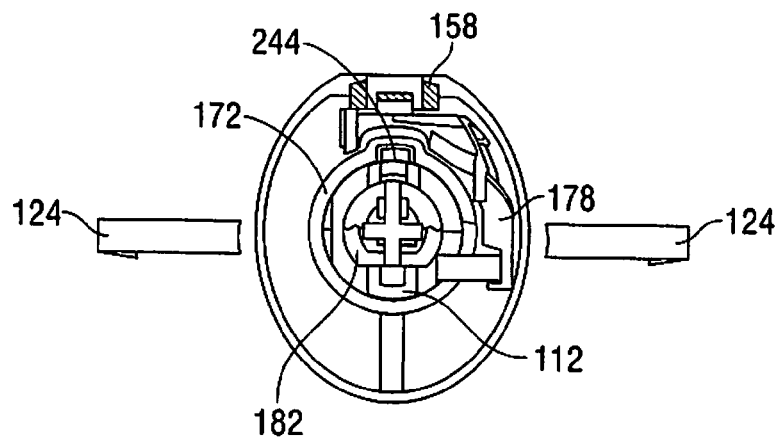
FIG. 19 is a transverse, cross-sectional view of the surgical retrieval apparatus of FIG. 1 similar to FIG. 17, wherein the plunger has been released.
Figure 20:
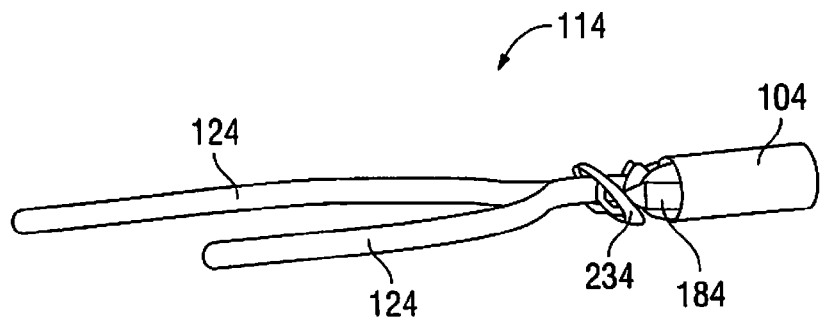
FIG. 20 is a front, perspective view of the end effector assembly of the specimen retrieval apparatus of FIG. 1 shown including an interference member disposed at a distal end of the sleeve.

Turning now to FIGS. 18-19, in conjunction with FIGS. 2-3, to permit translation of shaft 112 back to the insertion (and removal) position, release trigger 158 is actuated, i.e., depressed. Actuation of release trigger 158 urges lever 178 downwardly. As lever 178 is urged downward, lever 178 eventually contacts distal finger 236 of plunger 160, urging distal finger 236 inwardly to disengage distal finger 236 of plunger 160 from aperture 191 defined within tubular member 182 of shaft 112. Once distal finger 236 of plunger 160 is disengaged from shaft 112, plunger 160 is automatically extended proximally from shaft 112. More specifically, plunger 160 may be biased, e.g., via a spring (not shown), or other biasing member, toward the retracted position such that, once distal finger 236 of plunger 160 is disengaged from shaft 112, plunger 160 is automatically extended proximally, e.g., to "pop-out" from shaft 112, under the bias of the spring (not shown). Plunger 160 is inhibited from extending completely from shaft 112 via the engagement of annular rim 254 of plunger 160 within tubular member 182 of shaft 112.

Upon actuation of release trigger 158, lever 178 also engages collar 172 and rotates collar 172 about longitudinal axis "X-X." More specifically, lever 178 contacts collar 172 upon depression of release trigger 158 to urge collar 172 to rotate about longitudinal axis "X-X" such that flange 173 of collar 172 is rotated out of contact with articulation arm 244 of clutch 188. With flange 173 rotated out of contact with articulation arm 244, articulation arm 244 is no longer biased into engagement with proximal hub 246 of articulation bar 222 (see FIG. 12). In other words, upon actuation of release trigger 158, lever 178 rotates collar 172 to disengage articulation arm 244 from articulation bar 222, thereby disengaging articulation mechanism 180 and inhibiting articulation of end effector assembly 114 via rotation of articulation wheel 156.

Turning now to FIGS. 18-21, once release trigger 158 has been actuated to release plunger 160, the clinician may grasp plunger 160 and pull proximally to translate shaft 112 through channel 106 back to the insertion (and removal) position. As mentioned above, shaft 112 is translated proximally back to the insertion position such that end effector assembly 114 is completely disposed within channel 106 and such that releasable latch 192 is exposed, i.e., such that releasable latch 192 is positioned proximally of housing 102 (as opposed to the extended position of shaft 112, wherein releasable latch 192 is positioned within housing 102). At the same time, proximal translation of shaft 112 relative to specimen retrieval bag 118 disengages specimen retrieval bag 118 from end effector assembly 114 and pulls cinch cord 126 proximally to cinch closed open end 120 of specimen retrieval bag 118. More specifically, due to the engagement of cinch cord 126 through loop 122 of specimen retrieval bag 118 at first end 128 thereof and within releasable latch 192 of shaft 112 at second end 130 thereof, cinch cord 126 is translated proximally relative to specimen retrieval bag 118 to close specimen retrieval bag 118 as shaft 112 is translated proximally back to the insertion (and removal) position. Further, an interference member, or ring 234 disposed at the distal end of elongated sleeve 104 inhibits specimen retrieval bag 118 from being retracted into elongated sleeve 104 upon proximal translation of end effector assembly 114, helping to ensure that specimen retrieval bag 118 is disengaged from end effector assembly 114. Accordingly, during translation of shaft 112 from the extended position back to the insertion (and removal) position, specimen retrieval bag 118 is retained in position as shaft 112 and, thus, cinch cord 126 are translated proximally relative to specimen retrieval bag 118 to close specimen retrieval bag 118.

Figure 21:
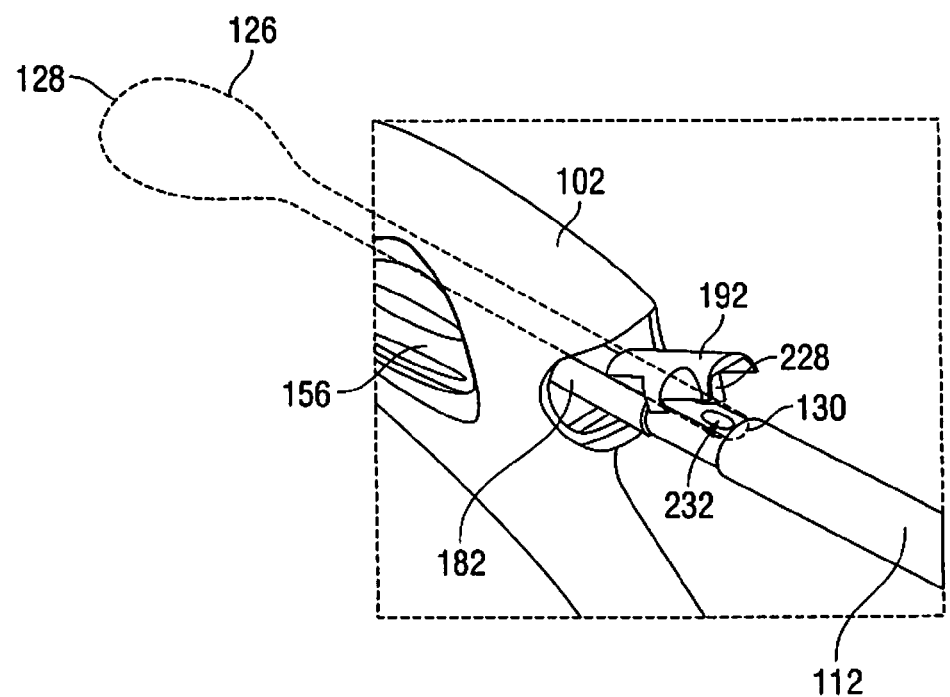
FIG. 21 is a rear, perspective view of the specimen retrieval apparatus of FIG. 1, wherein the shaft has been returned to the insertion position and wherein a releasable latch has been opened to disengage the cinch cord of the specimen retrieval bag from the specimen retrieval apparatus.

As shown in FIG. 21, releasable latch 192 may then be moved from the closed condition to the open condition to release cinch cord 126 from shaft 112, thereby disengaging specimen retrieval bag 118 from surgical retrieval apparatus 10. Thereafter, surgical retrieval apparatus 10 and the closed specimen retrieval bag 118 including the tissue specimen "S" disposed therein may each be removed, independently of one another, from the thoracic cavity.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical retrieval apparatus, comprising:
    a housing defining a longitudinal axis and including an elongated sleeve extending distally therefrom, the housing and the elongated sleeve cooperating to define a lumen extending longitudinally therethrough;
    a shaft having an end effector assembly disposed at a distal end thereof, the shaft slidably disposed within the lumen and selectively translatable through the lumen between a first position, wherein the end effector assembly is disposed within the elongated sleeve, and a second position, wherein the end effector assembly extends distally from the elongated sleeve;
    an articulation mechanism including an articulation member operably coupled to the end effector assembly and an articulation actuator operably coupled to the housing, the articulation member selectively movable relative to the end effector assembly to articulate the end effector assembly relative to the longitudinal axis, the articulation mechanism transitionable between a disengaged state, wherein the articulation actuator is disengaged from the articulation member, and an engaged state, wherein the articulation actuator is operably engaged with the articulation member, wherein, in the engaged state, actuation of the articulation actuator effects movement of the articulation member relative to the end effector assembly to articulate the end effector assembly relative to the longitudinal axis, and wherein translation of the shaft from the first position to the second position transitions the articulation mechanism from the disengaged state to the engaged state; and
    a specimen retrieval bag supported by the end effector assembly, the specimen retrieval bag deployable from an undeployed position to an open position.

2. The surgical retrieval apparatus according to claim 1, wherein the articulation actuator includes an articulation wheel rotatably mounted on the housing and wherein the articulation member includes an articulation bar slidably disposed within the shaft and operably coupled to the end effector assembly, the articulation wheel coupled to the articulation bar in the engaged state such that rotation of the articulation wheel relative to the housing translates the articulation bar through the shaft and relative to the end effector assembly to articulate the end effector assembly relative to the longitudinal axis.

3. The surgical retrieval apparatus according to claim 2, further comprising:
    a clutch coupled to the articulation wheel such that rotation of the articulation wheel effects longitudinal translation of the clutch, the clutch including an engagement arm configured to engage the articulation bar; and
    a collar configured to bias the engagement arm of the clutch into engagement with the articulation bar upon translation of the shaft from the first position to the second position.

4. The surgical retrieval apparatus according to claim 1, wherein articulation of the end effector assembly is inhibited when the shaft is disposed in the first position.

5. The surgical retrieval apparatus according to claim 1, further comprising a release trigger configured, upon actuation, to permit manual translation of the shaft from the second position back to the first position, wherein upon actuation, the release trigger transitions the articulation mechanism to the disengaged state.

* * * * *